(12) United States Patent
Pahan

(10) Patent No.: US 11,045,545 B2
(45) Date of Patent: Jun. 29, 2021

(54) IL-12 P40 MONOMER, MONOCLONAL ANTIBODY AGAINST P40 HOMODIMER AND THE COMBINATION OF THE TWO FOR AUTOIMMUNE DISEASE TREATMENT

(71) Applicant: Rush University Medical Center, Chicago, IL (US)

(72) Inventor: Kalipada Pahan, Skokie, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 16/130,787

(22) Filed: Sep. 13, 2018

(65) Prior Publication Data

US 2019/0008960 A1 Jan. 10, 2019

Related U.S. Application Data

(62) Division of application No. 14/118,698, filed as application No. PCT/US2012/038754 on May 21, 2012, now abandoned.

(60) Provisional application No. 61/487,744, filed on May 19, 2011.

(51) Int. Cl.
  *A61K 39/395* (2006.01)
  *A61K 38/20* (2006.01)
  *C07K 16/24* (2006.01)

(52) U.S. Cl.
  CPC ........ *A61K 39/3955* (2013.01); *A61K 38/208* (2013.01); *C07K 16/24* (2013.01)

(58) Field of Classification Search
  None
  See application file for complete search history.

(56) References Cited

U.S. PATENT DOCUMENTS 5,650,492 A 7/1997 Gately et al.
2007/0154453 A1 7/2007 Webster et al.

FOREIGN PATENT DOCUMENTS

| DE | 4315127 A1 | 11/1994 |
|---|---|---|
| WO | WO 1995/024918 | 9/1995 |
| WO | WO 1997/020062 | 6/1997 |
| WO | WO 2010/017598 A1 | 2/2010 |
| WO | WO 2012/159100 A1 | 11/2012 |

OTHER PUBLICATIONS

Costa et al. The Journal of Immunology 167:2379-2387 (Year: 2001).*
Dasgupta, Subhajit et al.; "Generation of Functional Blocking Monoclonal Antibodies against Mouse Interleukin-12 p40 Homodimer and Monomer"; Hybrodoma, vol. 27, No. 3; pp. 141-151; 2008.
Mondal, Susanta et al.; "Functional Blocking Monoclonal Antibodies against IL-12p40 Homodimer Inhibit Adoptive Transfer of Experimental Allergic Encephalomyelitis"; J Immulol., 182(8); pp. 5013-5023; Apr. 15, 2009.
International Search Report completed Jun. 25, 2012 for International Application No. PCT/US2012/038754.
Gately et al.; "The Interleukin-12/interleukin12-receptor system: role in normal and pathologic immune responses"; Annual Review of Immunology, vol. 16; Apr. 1998; pp. 495-521; Abstract.
Yoon et al.; "Charged residues dominate a unique interlocking topography in the heterodimeric cytokine interleukin-12"; The EMBO Journal, vol. 19, No. 14; Jul. 17, 2000; pp. 3530-3541.
BD Biosciences; Purified,NA/LE,Rat,Anti-Mouse,IL-12,(p40/p70),C17.8,RUO—554475; pp. 1-5; Jun. 3, 2020.

* cited by examiner

*Primary Examiner* — Gary B Nickol
*Assistant Examiner* — Jegatheesan Seharaseyon
(74) *Attorney, Agent, or Firm* — Taft Stettinius & Hollister LLP; Joseph M. Bennett-Paris

(57) ABSTRACT

A novel approach to discover new drugs against MS and other autoimmune diseases is disclosed. The p40 family of cytokines has four members which include interleukin-12 (IL-12), the p40 monomer (p40), the p40 homodimer ($p40_2$), and the IL-23. To facilitate the studies on $p40_2$ and p40, neutralizing monoclonal antibodies (mAb) against mouse $p40_2$ and p40 were generated for the first time. MS and other autoimmune disease drug therapies including recombinant p40 and/or monoclonal antibody against $p40_2$ (mAb-$p40_2$ a3-1d) are disclosed.

8 Claims, 7 Drawing Sheets

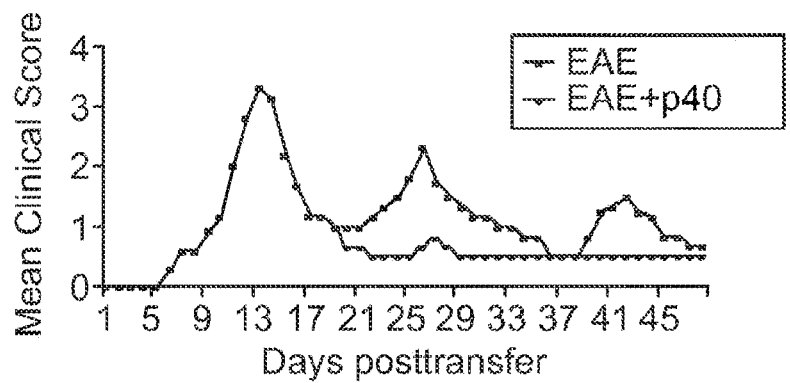
FIG. 1D
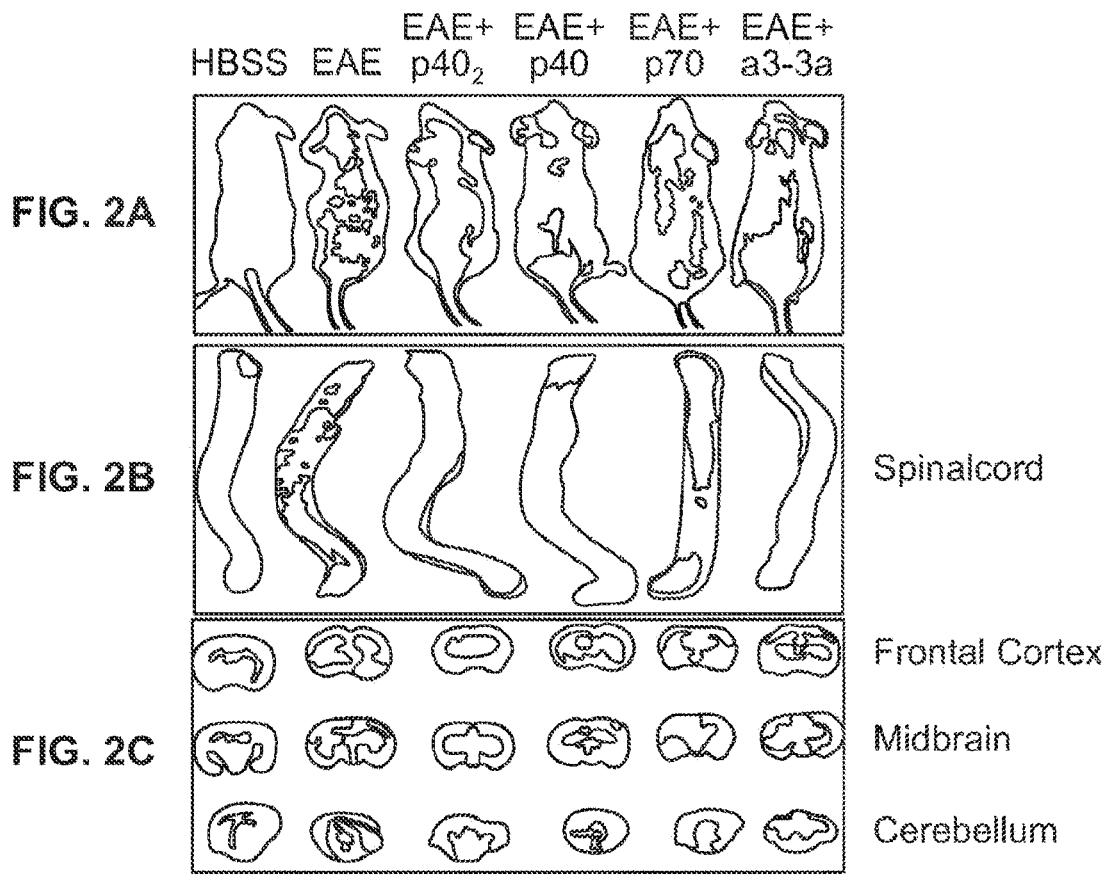

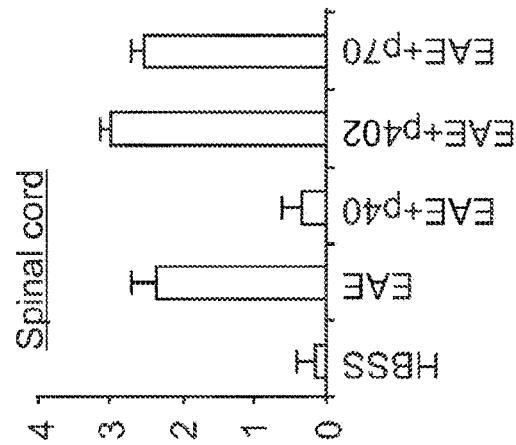
FIG. 3C
FIG. 3D
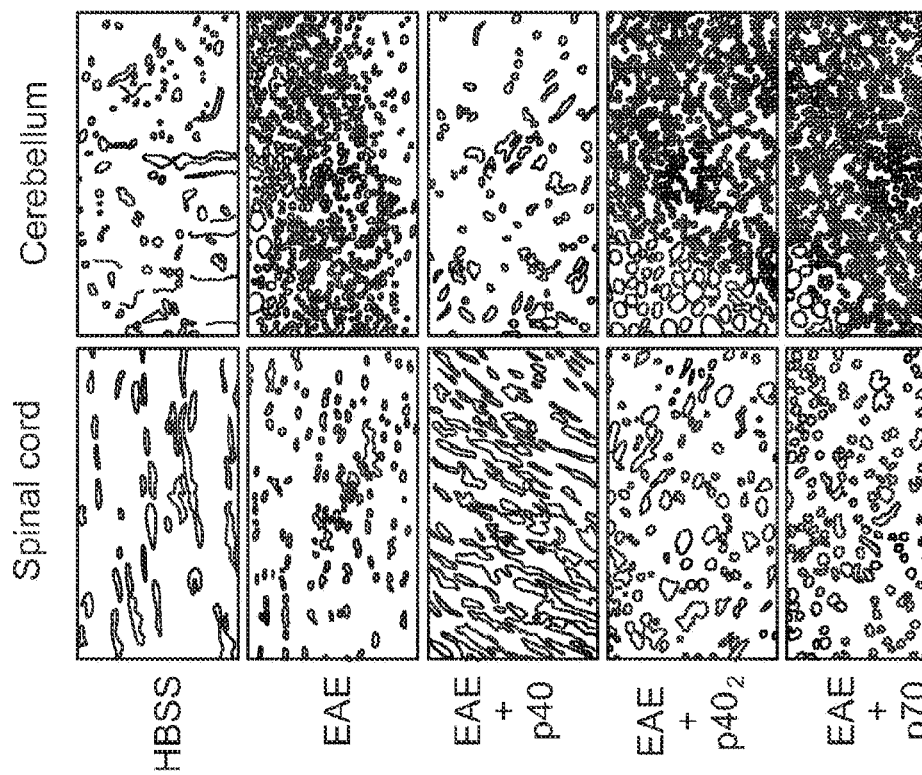
FIG. 3A
FIG. 3B

IL-12 P40 MONOMER, MONOCLONAL ANTIBODY AGAINST P40 HOMODIMER AND THE COMBINATION OF THE TWO FOR AUTOIMMUNE DISEASE TREATMENT

RELATED APPLICATIONS

This application is a division of application Ser. No. 14/118,698, filed May 28, 2014, which claims the benefit under 35 U.S.C. § 371 of International Application No. PCT/US2012/038754, filed May 21, 2012, which claims the benefit of U.S. Provisional Application No. 61/487,744, filed May 19, 2011, which are incorporated by reference herein in their entirety.

FEDERALLY SPONSORED RESEARCH OR DEVELOPMENT

This invention was made with government support under Grant No. NS039940, awarded by the National Institutes of Health. The Government has certain rights in the invention.

BACKGROUND

1. Technical Field Text

This disclosure relates to new drugs for the treatment of autoimmune diseases such as multiple sclerosis (MS), systemic lupus erythematosus (lupus), thyrioditis, rheumatoid arthritis, Sjogren's syndrome, Addison's disease etc.

2. Description of the Related Art

Multiple sclerosis (MS) is the most common human demyelinating disease of the central nervous system (CNS). Despite intense investigations, no effective therapy is available to stop its onset or halt its progression. MS is one of many autoimmune diseases and is a chronic human demyelinating disorder of the CNS of unknown etiology. From a clinical standpoint, MS is characterized by recurrent attacks of neurologic dysfunction. Pathologically, it can be identified by the presence of diffuse, discrete demyelinated areas, called plaques. MS is now widely viewed as an autoimmune disease that develops early in life (between the young ages of 20 and 40), perhaps after an unknown infection that initiates a T-cell mediated immune response.

Despite extensive research to develop pharmacotherapeutic agents to ameliorate exacerbations and to reduce the number of exacerbations and subsequent progression of neurologic disability in MS, only a few therapies are available, which are not very efficient. There is also a lack of effective therapies for other autoimmune diseases such as systemic lupus erythematosus (lupus), thyrioditis, rheumatoid arthritis, Sjogren's syndrome, Addison's disease etc., as well.

SUMMARY OF THE DISCLOSURE

A novel approach to discover new drugs against autoimmune diseases is disclosed.

The p40 family of cytokines has four members which include (1) interleukin-12 (IL-12), (2) the p40 monomer (p40), (3) the p40 homodimer ($p40_2$), and (4) the IL-23. Previously, with the knowledge that the heterodimers rule and the homodimers remain as mere spectators, those skilled in the art thought that only IL-23 and IL-12 were endowed with biological functions. Both $p40_2$ and p40 were considered as inactive molecules with unknown functions. To facilitate the studies on $p40_2$ and p40, neutralizing monoclonal antibodies (mAb) against mouse $p40_2$ and p40 were generated for the first time.

With experimental allergic encephalomyelitis (EAE) as the established animal model for MS, IL-12 p40 homodimer ($p40_2$) and p40 monomer (p40) were considered as inactive or inhibitory molecules and functions of these molecules were poorly understood.

After neutralizing mAb against mouse p40 and $p40_2$, the effect of $p40_2$, p40, mAb-$p40_2$, and mAb-p40 was tested on the disease process of EAE. While the recombinant p40 ameliorated clinical symptoms and disease progression of EAE, the mAb-p40 aggravated the disease process of EAE. On the other hand, the mAb-$p40_2$ protected mice from EAE and the recombinant $p40_2$ worsened the disease process of EAE. Furthermore, a combination of recombinant p40 and mAb-$p40_2$ strongly inhibited clinical symptoms of EAE. Taken together, our exciting results suggest the following new treatment options for MS patients: recombinant p40; monoclonal antibody against $p40_2$ (mAb-$p40_2$); and combinations of recombinant p40 and mAb-$p40_2$.

Therefore, in one aspect, a treatment for autoimmune diseases is disclosed which includes recombinant space p40.

In another aspect, a treatment for autoimmune diseases is disclosed which includes at least one monoclonal antibody against $p40_2$ (mAb-$p40_2$ a3-1d).

In yet another aspect, a treatment for autoimmune diseases is disclosed which includes a combination of recombinant p40 and at least one monoclonal antibody against $p40_2$ (mAb-$p40_2$ a3-1d).

In any one or more of the embodiments described above, the autoimmune disease may be selected from the group consisting of multiple sclerosis, lupus, thyrioditis, rheumatoid arthritis, Sjogren's syndrome, Addison's disease and combinations thereof.

In another aspect, a method for treating an autoimmune disease in a mammal is disclosed which includes administering recombinant p40 to the mammal.

In yet another aspect, a method for treating an autoimmune disease in a mammal is disclosed which includes administering at least one monoclonal antibody against $p40_2$ (mAb-$p40_2$ a3-1d) to the mammal.

In yet another aspect, a method for treating an autoimmune disease in a mammal includes administering a combination of recombinant p40 and at least one monoclonal antibody against $p40_2$ (mAb-$p40_2$ a3-1d).

Other advantages and features will be apparent from the following detailed description when read in conjunction with the attached drawings.

BRIEF DESCRIPTION OF THE DRAWINGS

FIGS. 1A-1D graphically illustrate the role of p40 monomer in the disease process of EAE.

FIGS. 2A-2C are photographs illustrating the effect of p40, $p40_2$, IL-12p70 and p40 mAb (a3-3a) on the integrity of BBB and BSB in EAE mice.

FIGS. 3A-3D illustrate photographically and graphically the effect of p40, $p40_2$, IL-12p70 on demyelination in the spinal cord and the cerebellum of EAE mice.

DETAILED DESCRIPTION OF THE PRESENTLY PREFERRED EMBODIMENTS

While the example below is directed towards MS, this disclosure applies to other autoimmune diseases such as systemic lupus erythematosus (lupus), thyroiditis, rheumatoid arthritis, Sjogren's syndrome, Addison's disease etc., as well.

Experimental allergic encephalomyelitis (EAE) is an experimentally induced autoimmune disease of the CNS, and serves as an animal model for MS. When the effect of recombinant p40₂ and p40 and neutralizing mAbs against p40₂ and p40 in EAE was tested, the following was observed.

IL-12 p40 Monomer Prevents MS-Like Autoimmune Demyelination in Mice

Figure 1A:
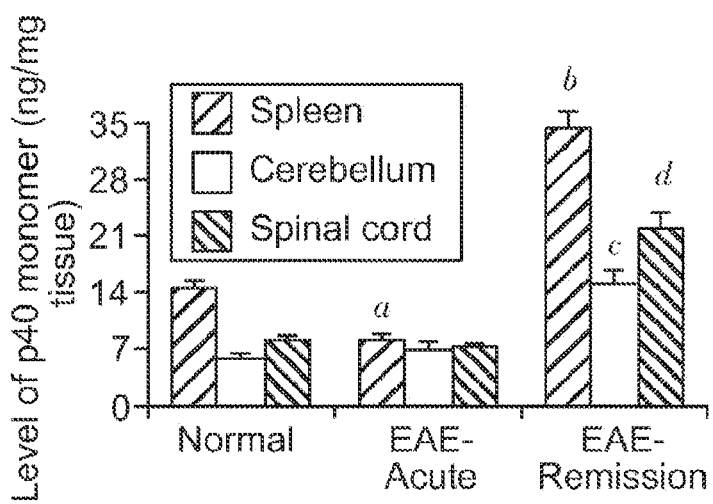

IL-12 and IL-23 are known to aggravate the disease process of EAE. To understand the role of p40 monomer in the disease process of EAE, first, the level of p40 in the spleen (the most important immune organ) of EAE mice was monitored at different phases of the disease. Surprisingly, the level of p40 was significantly lower in spleen of EAE mice at the acute phase compared with control (FIG. 1A). On the other hand, the level of p40 was very high in spleen during the remission phase (FIG. 1A) suggesting that p40 may have a protective role in EAE. Accordingly, the effectiveness of p40 in treating the disease process of EAE in mice (FIG. 1B) is demonstrated.

To understand the effect of p40 on disease progression, mice with established disease received weekly intraperitoneal injection of p40 monomer from different phases of the disease. When administered from the onset of acute phase (8 days post transfer), p40 markedly suppressed clinical symptoms (FIG. 1C). In contrast to native p40, heat-inactivated p40 had no protective effect on EAE (FIG. 1C), suggesting the specificity of the effect. On the other hand, p40 mAb a3-3a aggravated the disease process (FIG. 1C). Again, p40 also protected mice from EAE when administered from the onset of relapsing phase (FIG. 1D).

Figure 1B:
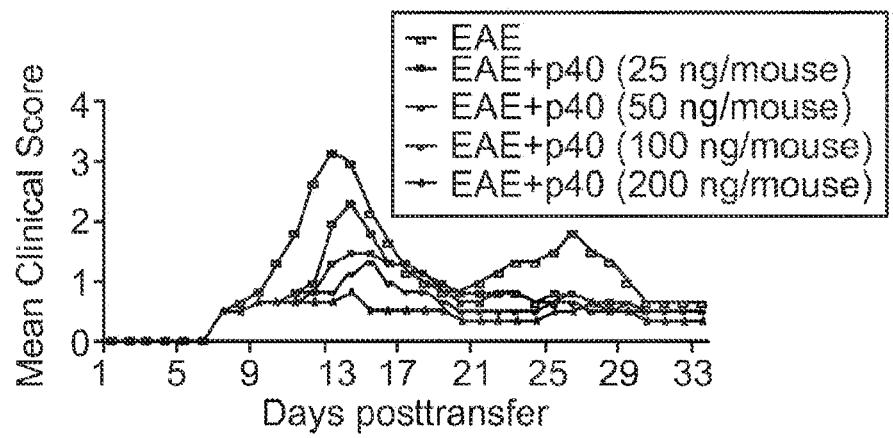
Figure 1C:
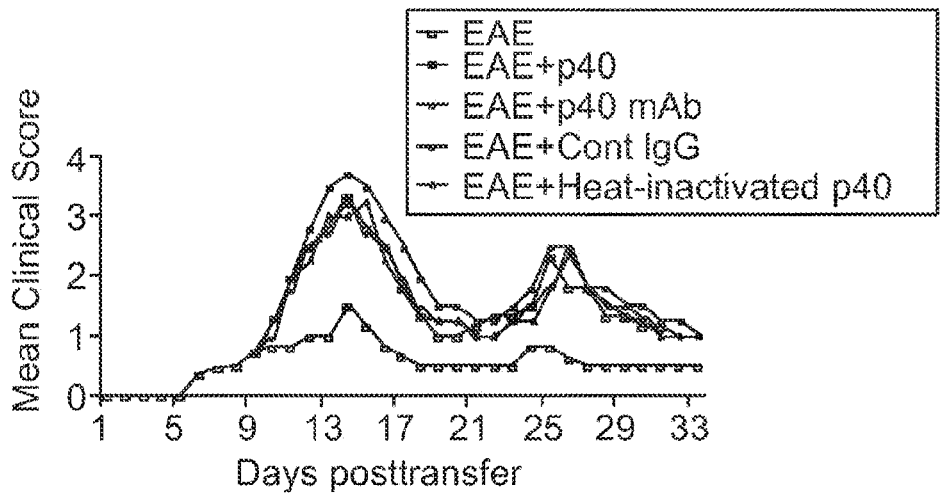

FIGS. 1A-1D illustrate the role of p40 monomer in the disease process of EAE. In FIG. 1A, the level of p40₂ was measured by ELISA in a spleen, cerebellum and spinal cord of mice with different phases of EAE. Results are mean±the standard deviation of three two separate analyses of three different mice. In FIG. 1B, female SJL/J mice were induced EAE by adoptive transfer of MBP-primed T cells. Initially or at 0 days of post transfer, the mice received a weekly injection (intraperitoneal) of different amounts of p40 monomer. The mice (n=6 in each group) were monitored daily for clinical symptoms. In FIG. 1C, from 8 days post transfer, the onset of acute phase, the mice (n=6) were treated with p40, mAb-p40 (a3-3a), control IgG, or heat-inactivated p40. In FIG. 1D, from 19 days post transfer, the onset of relapsing phase, mice (n=6) were treated with p40. Mice (n=6) were monitored daily for clinical symptoms.

Histological and blood-brain barrier (BBB) and blood-spinal cord barrier (BSB) permeability studies reveal that p40 effectively inhibited the infiltration of mononuclear cells into brain and spinal cord (FIG. 2), protected myelin (FIG. 2) and improved the integrity of BBB and BSB in EAE mice (FIG. 3).

In FIGS. 2A-2C, the effect of p40, p40₂, IL-12p70, and p40 mAb (a3-3a) on the integrity of BBB and BSB in EAE mice is illustrated. In FIG. 2A, HBSS-treated control mice and different groups of EAE mice (n=4 in each group) received 200 μl of 20 μM Alexa Fluor 680-SE-NIR dye (Invitrogen) via the tail vein on 15 days post transfer (acute phase). After 2 hours, the mice were scanned in an Odyssey (ODY-0854; Licor) infrared scanner at the 700 and 800-nm channels. The mice were perfused with 4% paraformaldehyde. In FIG. 2B the spinal cord and in FIG. 2C, different regions of brain were scanned in an Odyssey infrared scanner. The red background came from an 800-nm filter, whereas the green signal was from Alexa Fluor 680 dye at the 700-nm channel.

In FIGS. 3A-3C the effect of p40, p40₂ and IL-12 p70 on demyelination in the spinal cord and cerebellum of EAE mice is illustrated. Longitudinal sections of spinal cord (FIG. 3A) and coronal sections of cerebellum (FIG. 3B) is isolated from HBSS-treated normal, EAE (15 days post transfer), p40-treated EAE, (15 days post transfer receiving p40 from 8 days post transfer), p40₂ treated EAE (15 days post transfer receiving p70 from 8 days post transfer) mice were stained with Luxol fast blue. Digital images were collected under brightfield settings using a ×40 objective. Demyelination in cerebellum (FIG. 3C) and spinal cord (FIG. 3D) are represented quantitatively. Data are expressed as the mean±the standard deviation of five different mice ($^a p<0.001$ vs EAE).

Therefore, p40 monomer may be beneficial for MS and other autoimmune disease patients.

Figure 4A:
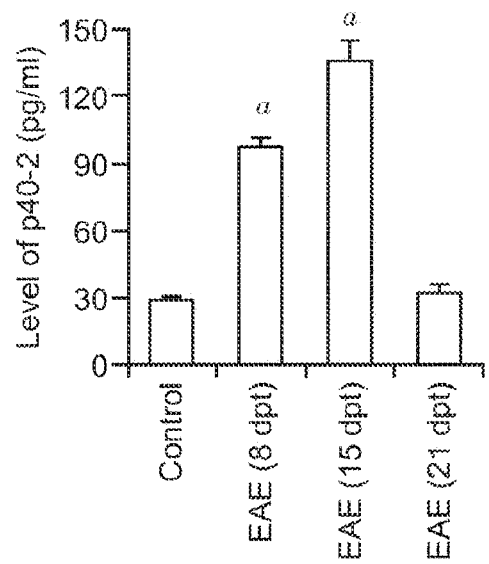
FIGS. 4A-4B illustrate graphically the level of $p40_2$ in the serum, spleen, cerebellum and spinal cord of mice with different phases of EAE.

Functional Blocking Monoclonal Antibodies (a3-1d) Against p40₂ Inhibit the Disease Process of EAE in Mice To understand the role of p40₂ in the disease process of EAE, the level of p40₂ in the serum and spleen of EAE mice at different phases of the disease was monitored. The level of p40₂ was significantly higher in serum of EAE mice at the onset of acute phase and the acute phase compared with control (FIG. 4A). However, the serum level of p40₂ was almost close to normal during the remission phase (FIG. 4A). Similarly, the level of p40₂ was also very high in spleen, cerebellum, and spinal cord during the acute phase of EAE (FIG. 4B) suggesting that p40₂ may play a role in the disease process of EAE. To test this hypothesis, mice with established EAE were treated with just one dose of p40₂ mAb (a3-1d) via intra-peritoneal injection.

Figure 4B:
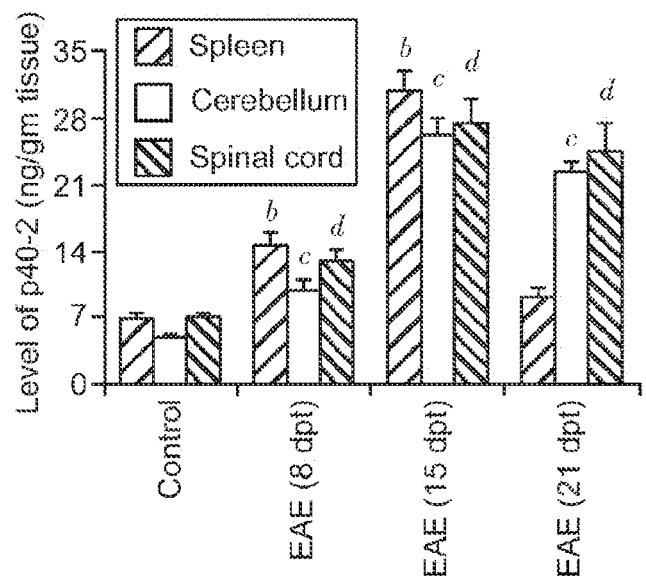

In FIGS. 4A and 4B, the levels of p40₂ in serum, spleen, cerebellum, and spinal cord of mice with different phases of EAE is illustrated. Female SJL/J mice were induced EAE by adoptive transfer of MBP-primed T cells. At different phases of the disease (8 days post transfer, the onset of acute phase; 15 days post transfer, the acute phase; 21 days post transfer, the remission phase), the level of p40₂ was measured in serum (FIG. 4A) and homogenates of spleen, cerebellum and spinal cord (FIG. 4B) by sandwich ELISA. Four mice (n=4) were used for each time point. The results shown are mean±the standard deviation of three different assays: $^a p<0.001$ vs control serum; $^b p<0.001$ vs control spleen; $^c p<0.001$ vs control cerebellum; and $^d p<0.001$ vs control spinal cord.

Figure 5A:
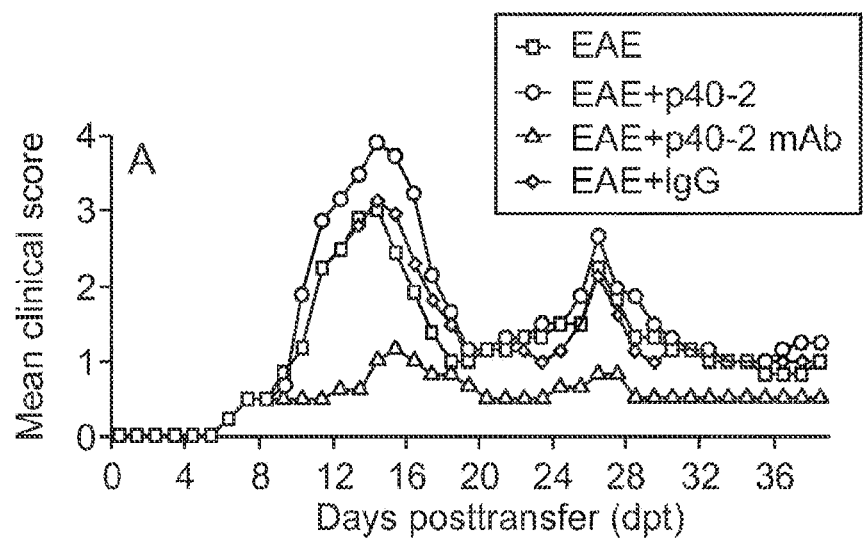
FIGS. 5A-5B illustrate graphically the treatment of adoptively transferred EAE in SJL/J mice by $p40_2$ and mAb against $p40_2$.
Figure 5B:
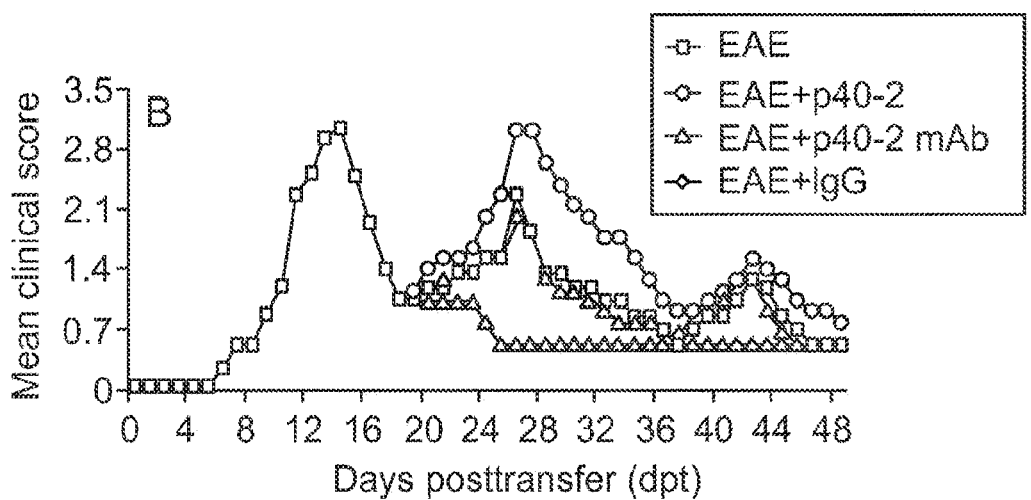
Figure 6A:
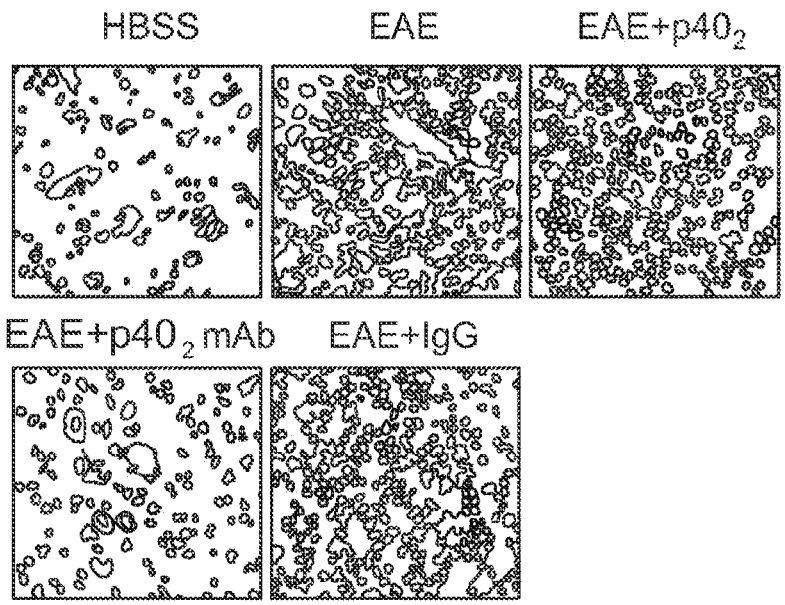
FIGS. 6A-6C illustrate photographically and graphically the effect of p40₂ mAB on the infiltration of mononuclear cells into the CNS of EAE mice.
Figure 6B:
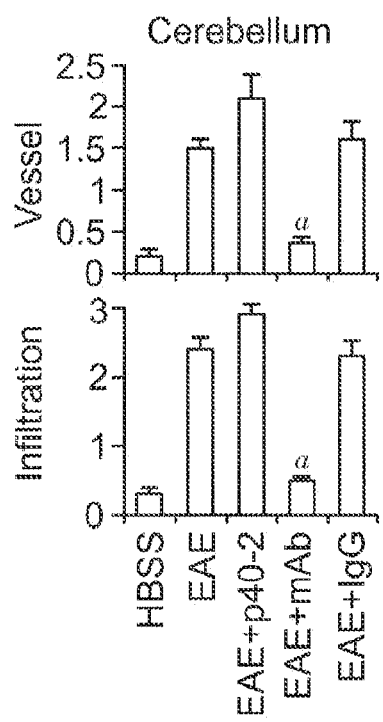
Figure 6C:
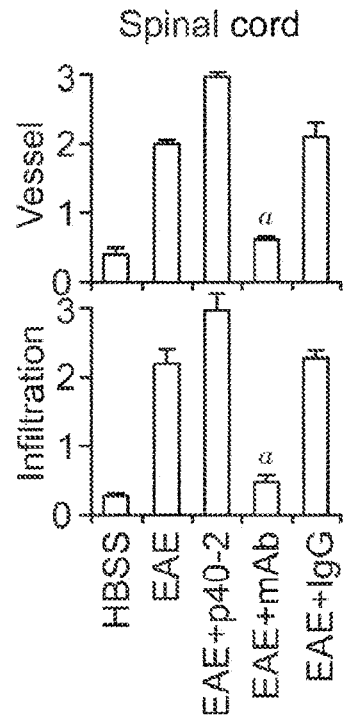

Within 4 days of injection, significant reduction in EAE clinical symptoms was found and, interestingly, just one injection kept disease symptoms markedly low throughout the duration of the study (FIGS. 5A-5B). In FIGS. 5A-5B, treatment of adoptively transferred EAE in SJL/J mice by p40$_2$ and mAb against p40$_2$ is illustrated. EAE was induced in female SJL/J mice by adoptive transfer of MBP-primed T cells. Group of EAE mice (n=6) were treated with p40$_2$ (200 ng/mouse), p40$_2$ mAb a3-1d (100 µg/mouse), or normal hamster IgG (100 µg/mouse) from the onset of acute phase (8 days post transfer) (FIG. 5A) and the onset of relapsing phase (18 days post transfer) (FIG. 5B). Mice were examined for clinical symptoms for the next 30 days. Histological and blood-brain barrier (BBB) and blood-spinal cord barrier (BSB) permeability studies reveal that p40$_2$ mAb effectively inhibited the infiltration of mononuclear cells into brain and spinal cord and improved the integrity of BBB and BSB in EAE mice (FIGS. 6A-6C). Consequently, p40$_2$ mAb also suppressed the expression of pro-inflammatory molecules, normalized the expression of myelin genes and blocked demyelination in the CNS of EAE mice.

In FIGS. 6A-6C the effect of p40$_2$ and p40$_2$ mAB on the infiltration of mononuclear cells into the CNS of EAE mice is illustrated. In FIG. 6A, cerebellar sections are isolated from HBSS-treated normal, control EAE (15 days post transfer), p40$_2$ treated EAE (15 days post transfer receiving p40$_2$ from 8 days post transfer), p40$_2$ mAb-treated EAE (15 days post transfer receiving p40$_2$ mAb from 8 days post transfer), and control IgG-treated EAE (15 days post transfer receiving control IgG from 8 days post transfer) mice were stained with H&E. Digital images were collected under brightfield setting using a ×40 objective. In FIGS. 6B and 6C, infiltration and cuffed vessel in cerebellar and spinal cord sections were represented quantitatively by using a scale as described above. Data are expressed as the mean±the standard deviation of five different mice ($^a$p<0.001 vs EAE).

On the other hand, recombinant mouse p40$_2$ cytokine aggravated the disease process of EAE (FIGS. 5A-5B and 6A-6C). These results suggest that neutralization of p40$_2$ by p40$_2$ mAb a3-1d may be beneficial in MS and other autoimmune disease patients.

Figure 7:
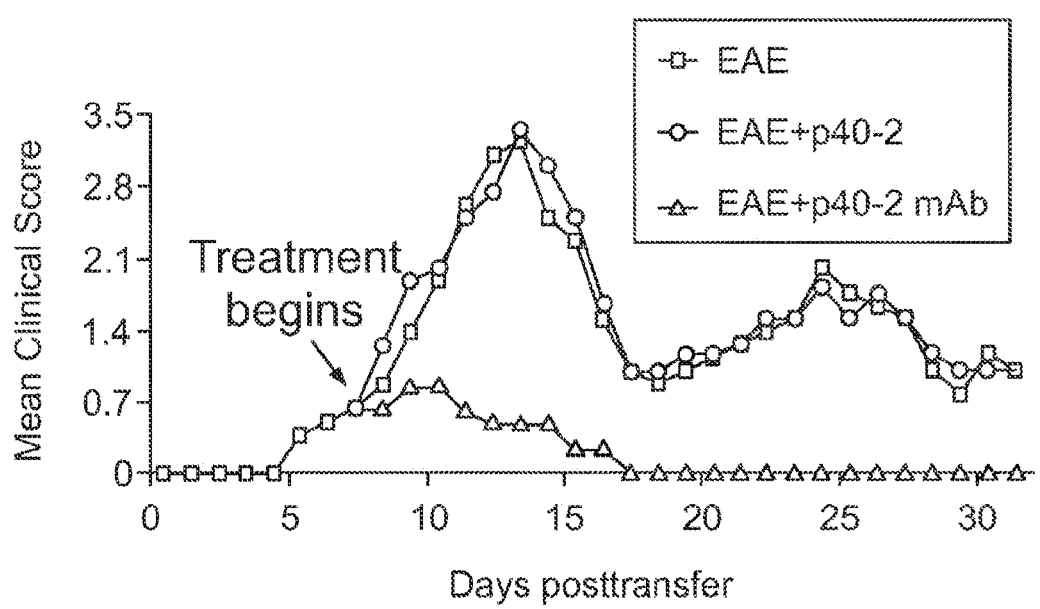
FIG. 7 illustrates graphically the treatment of adoptively-transferred EAE in SJL/J mice by the combination of p40 monomer and the mAB against p40₂.

Combination of p40 Monomer and p40$_2$ mAb a3-1d Strongly Suppresses the Disease Process of EAE Since both p40 and mAb p40$_2$ inhibited the disease process of EAE, the combination of the two were investigated to see if they show better efficacy. Therefore, mice and with established disease received one injection of p40$_2$mAb a3-1d and a weekly injection of p40 monomer. As shown in FIG. 7, this combination strongly suppressed clinical symptoms of EAE. On the other hand, the combination of control IgG and saline had no effect (FIG. 7) suggesting the specificity of the effect.

In FIG. 7, the treatment of adoptively-transferred EAE in SJL/J mice by the combination of p40 monomer and mAb against p40$_2$ is illustrated. EAE was induced in female SJL/J mice by adoptive transfer of MBP-primed T cells. Groups of EAE mice (n=6) were treated with the combination of p40 (100 ng/mouse/week) and p40$_2$ mAb a3-1d (100 µg/mouse), or the combination of normal saline and control hamster IgG (100 µg/mouse) from the onset of acute phase (8 days post transfer). The mice were examined for clinical symptoms for 32 days.

Therefore, this combination may be a strong blocker of MS symptoms in patients.

Taken together, these novel results suggest the following three new treatment options for MS and other autoimmune disease patients: recombinant p40; monoclonal antibody against p40$_2$ (mAb-p40$_2$a3-1d); and a combination of recombinant p40 and mAb-p40$_2$ (a3-1 d).

Under the provisions of the Budapest Treaty on the International Recognition of the Deposit of Microorganisms for the Purpose of Patent Procedure, Applicant has deposited biological material comprising twenty-five (25) vials of hybridoma with the designation of antibody (mAb)a3-1d with the International Depositary Authority, American Type Culture Collection (ATCC) of 1080 University Blvd., Manassas, Va. 20110-2209, on Dec. 3, 2020 and assigned deposit number PTA-126900. The deposited hybidoma comprises a monoclonal antibody against the p40$_2$ homodimer which comprises mAb-p40$_2$ a3-1d.

While only certain embodiments have been set forth, alternatives and modifications will be apparent from the above description to those skilled in the art. These and other alternatives are considered equivalents and within the spirit and scope of this disclosure and the appended claims.

The invention claimed is:

1. A method for treating an autoimmune disease in a mammal, the method comprising: administering a combination of a recombinant p40 monomer protein and at least one monoclonal antibody against p40$_2$ homodimer to the mammal for treating an autoimmune disease in the mammal, wherein the at least one monoclonal antibody against the p40$_2$ homodimer comprises mAb-p40$_2$ a3-1d.

2. The method of claim 1, wherein the recombinant p40 monomer protein is administered in a plurality of doses.

3. The method of claim 1, wherein the at least one monoclonal antibody against p40$_2$ homodimer is administered in a single dose.

4. The method of claim 1, wherein the recombinant p40 monomer is administered in a plurality of doses and the at least one monoclonal antibody against p40$_2$ homodimer is administered in a single dose.

5. The method of claim 1, wherein the administration ameliorates one or more of symptoms of the autoimmune disease, the one or more symptoms comprising demyelination, blood-brain barrier permeability, blood-spinal cord barrier permeability and combinations thereof.

6. The method of claim 1, wherein the administration ameliorates one or more of the autoimmune diseases selected from the group consisting of multiple sclerosis, lupus, thyroiditis, rheumatoid arthritis, Sjogren's syndrome, Addison's disease and combinations thereof.

7. The method of claim 1, wherein the at least one monoclonal antibody against p40$_2$ homodimer is administered in a plurality of doses.

8. The method of claim 1, wherein the recombinant p40 monomer is administered in a plurality of doses and the at least one monoclonal antibody against p40$_2$ homodimer is administered in a plurality of doses.

* * * * *